United States Patent [19]

Obser et al.

[11] 4,004,153

[45] Jan. 18, 1977

[54] APPARATUS FOR MONITORING A WEB OF MATERIAL

[75] Inventors: Werner Obser, Geretsried; Gernot Pinior, Olching, both of Germany

[73] Assignee: Erwin Sick GmbH Optik-Elektronik, Waldkirch, Germany

[22] Filed: July 7, 1975

[21] Appl. No.: 593,400

[30] Foreign Application Priority Data

July 12, 1974 Germany .................... 2433682

[52] U.S. Cl. .............................. 250/572; 250/226; 356/200

[51] Int. Cl.[2] ...................................... G01N 21/32

[58] Field of Search ........... 250/571, 572, 562, 563, 250/216, 227, 226; 386/237, 238, 239, 199, 200

[56] References Cited

UNITED STATES PATENTS

| | | | |
|---|---|---|---|
| 3,060,319 | 10/1962 | Greunke | 250/571 |
| 3,198,951 | 8/1965 | Lentze | 250/563 |
| 3,317,738 | 5/1967 | Piepembrink et al. | 250/572 X |
| 3,331,963 | 7/1967 | Lippke | 250/563 |
| 3,574,469 | 4/1971 | Emerson | 250/571 X |
| 3,784,832 | 1/1974 | Sewell | 250/226 |

*Primary Examiner*—Alfred E. Smith
*Assistant Examiner*—T. N. Grigsby
*Attorney, Agent, or Firm*—Townsend and Townsend

[57] ABSTRACT

Apparatus for monitoring a web of material for faults which affect the remission and/or reflection of light incident on the material. Light from two light sources, one emitting light of a narrow spectral band width and one emitting light of a broad spectral band width, are projected onto the web in the form of two at least overlapping light spots and so that the light spot of the former source is relatively smaller than the light spot of the latter source. Light remitted and/or reflected by the web is concentrated on light receiving rods for transmission to photo-multipliers mounted to end faces of the rods. The light from the respective sources is suitably filtered so that each photo-multiplier receives only light from one source. In an alternative embodiment the remitted light is transmitted to a single photo-multiplier which simultaneously receives light from both sources.

22 Claims, 5 Drawing Figures

APPARATUS FOR MONITORING A WEB OF MATERIAL

BACKGROUND OF THE INVENTION

The invention relates to an apparatus for monitoring a web of material or some other scanning plane relative to faults which influence the remission and/or reflection of a striking beam of transmitted light, whereby a beam of transmitted light scanning the width of a web of material at right angles to its direction of movement is concentrated on the web by a cylindrical lens and light reflected back by the web is projected onto a light guide rod on whose face or faces are provided one or two photosensitive devices.

The object of a simultaneously filed application by the same inventors for APPARATUS FOR MONITORING A MOVING WEB OF MATERIAL FOR FAULTS, the disclosure of which is incoporrated by reference in the present application comprises increasing the significance of the electrical signals obtained, thereby permitting a better differentiation between different types of fault. The parallel application deals substantially with the received beam path and provides an optical arrangement permitting a better classification of the nature of the faults in that both reflected and remitted light are used for evaluation purposes, whereby optionally different spectral ranges can also be used. Thus, a total of two or four electrical signals are available for fault evaluation.

BRIEF SUMMARY OF THE INVENTION

The problem of the present invention is more particularly to form the transmitted beam path in such a way that maximum universality also exists from this side when characterizing faults.

According to the present invention this problem is solved in that the light of the transmitted light beam is mixed from the light of two different light sources. In this connection, one light source advantageously has a very narrow spectral range whilst the other has a wide spectral range. Whilst the narrow-band light source is preferably a laser and more specifically an He-Ne-gas laser the wide-band light source is advantageously a xenon high pressure lamp.

This permits a further differentiation of different faults, whilst permitting the utilisation for fault evaluation of both the differing response of the faults to a wide-band light beam on the one hand and a wide-band light beam on the other.

It is particularly advantageous in this connection if different but at least overlapping light spots are projected by the two light sources in the scanning plane. The light spot projected by the narrow-band light source must be smaller than that of the light spot projected by the wide-band light source and must be contained in the latter. Whereas the light spot of the wide-band light source is advantageously substantially rectangular and preferably square, the light spot of the narrow-band light source is substantially elliptical.

The relatively small laser light spot is particularly suitable for recognizing small faults such as scratches, whilst the relatively large light spot of the xenon lamp permits the recognition of large chromatic faults.

Whilst for the fusion of the two rays, any ray fusion device known for this purpose can be used, the light of the different light sources is preferably passed from opposite sides onto a crossed mirror, whereby the laser light advantageously strikes the inner, narrow mirror of the set of crossed mirrors.

As is more particularly described in the parallel application, remitted and reflected light is preferably received by different light guide rods. However, the present invention retains its significance if only one light guide rod is used for reflected or remitted light.

Advantageously, and preferably, at the ends of the light guide rods photosensitive devices are provided, sensitive through color filters in different spectral ranges. Advantageously, only a partial range of the xenon high pressure lamp spectrum is used through arranging a color filter only permitting the passage of a spectral range from 350 to 650 nm on the xenon high pressure lamp prior to the fusion of the ray with the laser light.

In practice, the construction is such that the color filters filter off the light of the xenon high pressure lamp at one end of the light guide rods and only transmit the laser light. The electrical signal emitted by the particular photoelectric devices can therefore be used for the recognition of very small faults such as, e.g., scratches.

In another practical construction, the color filters at the other end of the light guide rods separate the laser light from the xenon light and only transmit the latter. The photoelectric devices arranged at the said ends consequently supply an electrical signal permitting the recognition of larger faults.

Preferably, the color filter located in front of the light guide rod which receives the remitted light is constructed in such a way that it can also be ommitted. The photosensitive device at this point then receives a mixture of prefiltered xenon light and laser light, so that chromatic faults can be recognized. The red laser is, e.g., blind for red spots on a white background.

According to the invention, a further possibility is provided in that in place of the cylindrical lens receiving the remitted light and the appropriate light guide rod, a photosensitive device arranged in an autocollimation beam is used which is sensitive for the light of both light sources.

This construction is characterized by structural simplicity and a considerable cost reduction. It permits the use of remitted mixed light formed from laser light and filtered xenon light for recognizing chromatic faults in the web of material.

BRIEF DESCRIPTION OF THE DRAWINGS

Other and further objects of the present invention will be apparent from the following description and claims and are illustrated in the accompanying drawings which by way of illustration show preferred embodiments of the present invention and the principles thereof and what are now considered to be the best modes contemplated for applying these principles. Other embodiments of the invention embodying the same or equivalent principles may be used and structural changes may be made as desired by those skilled in the art without departing from the present invention and the scope of the appended claims. In the drawings show:

DETAILED DESCRIPTION OF THE PREFERRED EMBODIMEMTS

Figure 1:
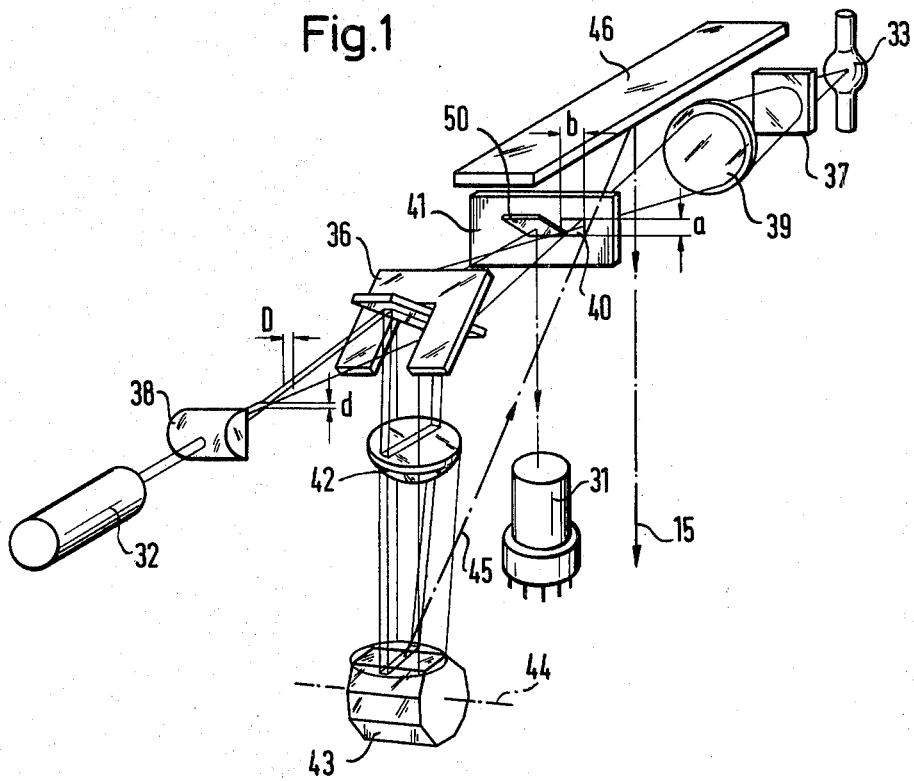
FIG. 1 a perspective view of the optical arrangement for forming a transmitted light beam from two different light sources.
Figure 2:
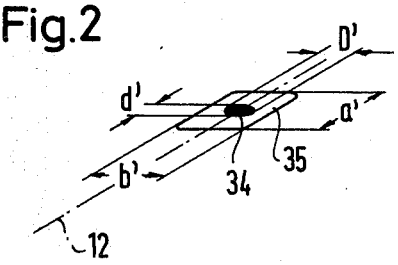
FIG. 2 a perspective view of the light spot preferably formed from the two light sources on the web of material or in the scanning plane.
Figure 3:
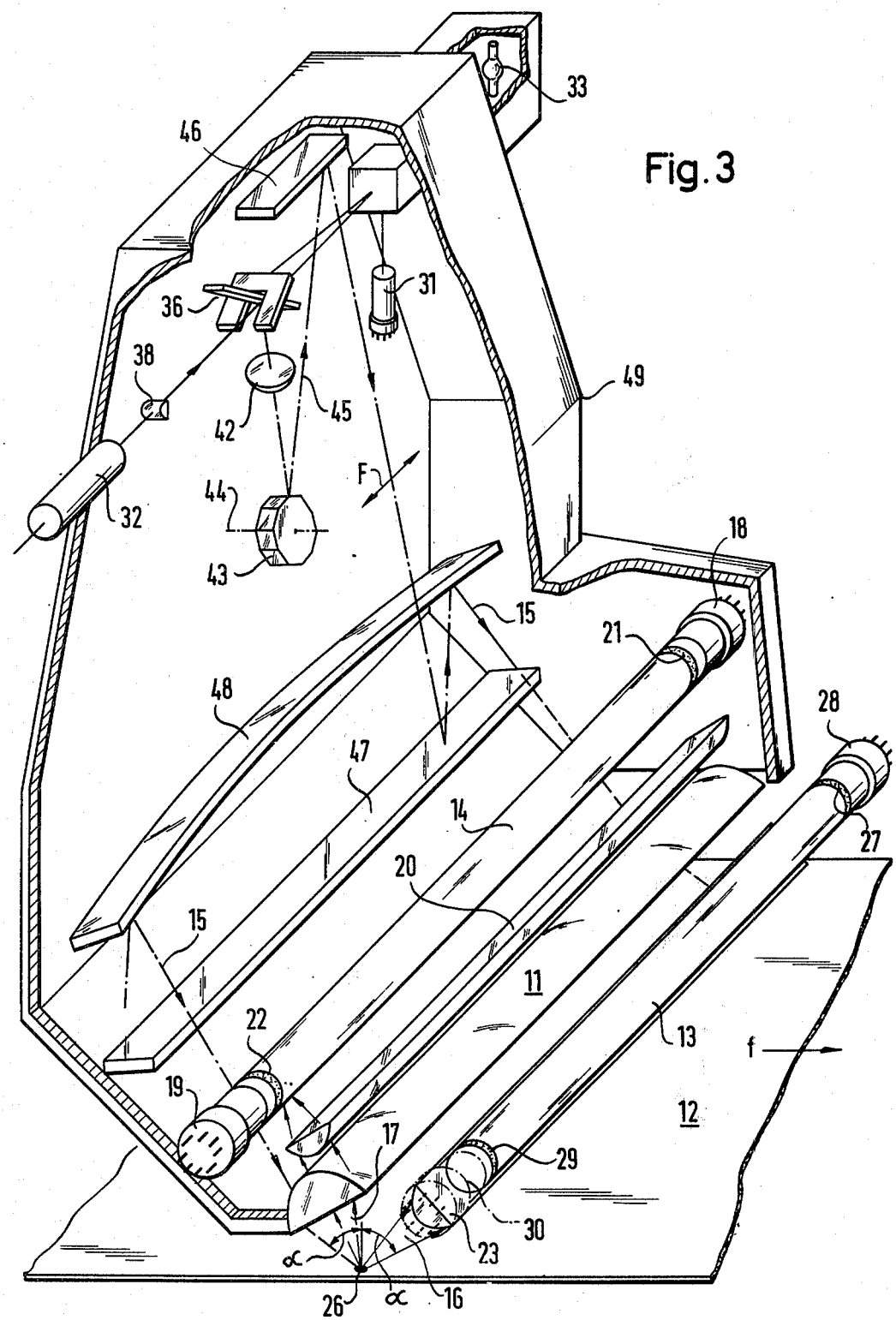
FIG. 3 a perspective view of the entire apparatus according to the invention comprising the transmitting portion and the receiving portion.

According to FIGS. 1 to 3, the light of a laser 32 is deflected by means of a cylindrical lens 38 in somewhat fanned out form onto the inside of a crossed mirror 36, which deflects the laser light vertically downwards at an angle of 90°.

Figure 4:
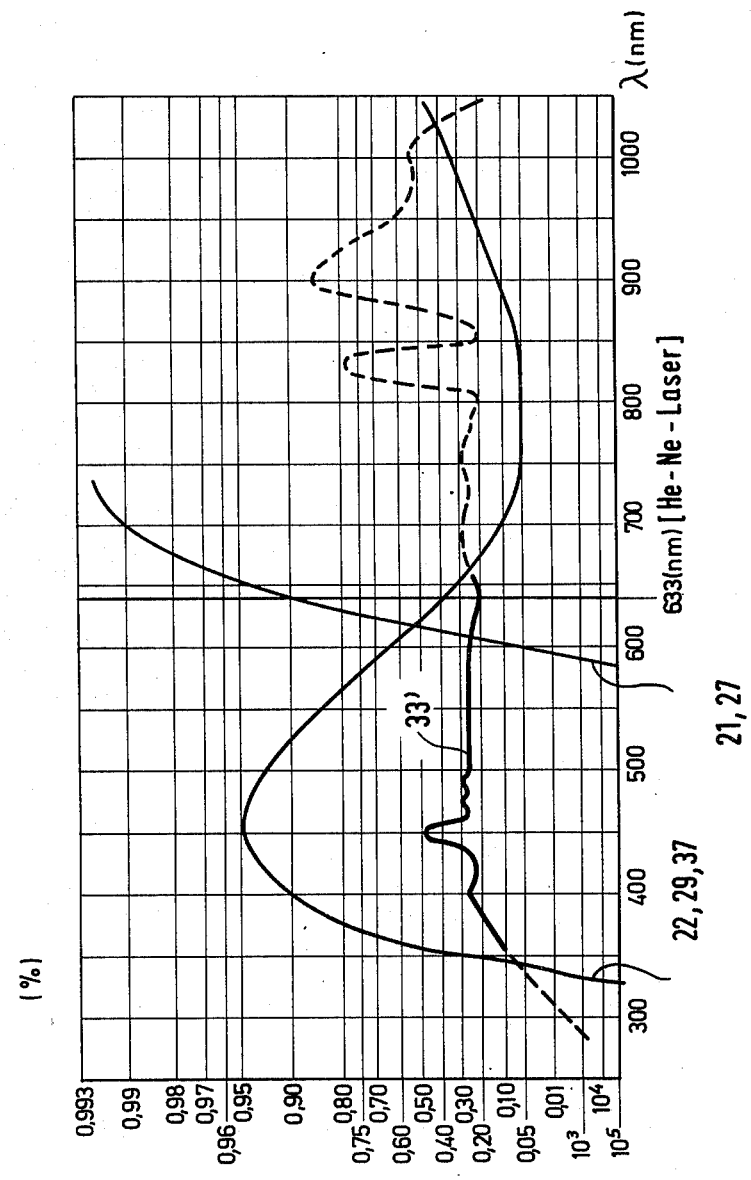
FIG. 4 a diagram showing the spectral ranges which are preferably used for the light sources and the filters employed.

On the opposite side, a xenon high pressure lamp 33 is provided, in front of which is positioned a color filter 37 whose spectral transmission is shown in FIG. 4. Behind color filter 37 is provided a condenser 39 which projects the light source into the rectangular aperture 40 of a diaphragm 41. From aperture 40, the xenon light passes to the outer areas of crossed mirror 36 which vertically downwardly deflects it to lens 42 located vertically below the crossed mirror 36.

According to the invention, beneath the lens is provided a per se known mirror wheel 43 whose centre of rotation 44 is substantially perpendicular to the plane defined by the rays deflected by 90°. However, the axis is tilted somewhat downwards in such a way that the light 45 reflected by the mirror wheel strikes against a plane mirror 46 located above the optical transmitting arrangement whose linear extension coincides with the scanning direction of mirror wheel 43. Plane mirror 46 downwardly deflects the light onto a further plane mirror 47 which extends substantially over the entire width of the apparatus. From plane mirror 47 the light is again reflected obliquely upwards to a strip-like concave mirror 48 whose focal point is located at the position of mirror wheel 43 and which finally deflects the transmitted light beam onto the cylindrical lens 11, also represented in the parallel application, and specifically into only half of its aperture. The concave mirror 48 gives a parallel direction to the light coming from one point on mirror wheel 43.

Cylindrical lens 11 contracts the parallel incoming transmitted light 15, perpendicular to scanning direction F onto a point 26 of material web 12, where there may be for example a fault to be analyzed. The cylindrical lens 11 is ineffective in scanning direction F.

The transmitted light beam 15 continuously scans the web of material perpendicular to its movement of direction, i.e., in the direction of double arrow F in accordance with FIGS. 2 and 3.

The right-hand half of cylindrical lens 11 in FIG. 3 is used to receive light 17 remitted by material web 12 and to direct it in a parallel direction. Thus, by pupillary spacing the cylindrical lens is used for both transmitted and received light.

A further cylindrical lens 20 parallel to the cylindrical lens 11 is arranged above the latter in the direction of the remitted light and concentrates the parallel light beam received by its whole cross-section onto the dispersed surface reception area of a light guide rod 14. By dispersion and total reflection within light guide rod 14 the light striking the surface area reaches two photoelectric devices 18, 19 which can, e.g., be photomultipliers arranged on the faces. Between the faces of light guide rod 14 and photomultipliers 18, 19 are provided color filters 21, 22 which are particularly important for the purposes of the present invention.

It is assumed that the emitted light beam strikes the web of material 12 at an angle $\alpha$. According to the invention, a further optical receiving device is then arranged at the opposite same angle $\alpha$ relative to the perpendicular on material web 12 which receives the reflected portion 16 of the incident light. This device comprises a cylindrical lens 23 which is parallel to the two other cylindrical lenses 11, 20 and deflects the reflected light 16 onto the dispersing surface reception area of a further light guide rod 13. This is constructed identically to light guide rod 14 and according to FIG. 3 also carries on its faces, color filters 27, 29 and photomultipliers 28, 30. To illustrate cylindrical lens 23 the photomultiplier 30 in FIG. 3 is only shown by dotted lines.

Whilst photomultipliers 18, 19 on light guide rod 14 provide a criterion for the remission capacity of the fault 26 on material web 12 struck by the transmitted light beam, at the faces of light guide rod 13 a signal can be received from the photoelectric devices 28, 30 which is representative for the reflection capacity of fault 26.

The whole arrangement is located in a casing 49 which has the shape shown in FIG. 3, but is broken open to illustrate the components located within the same.

As can be gathered particularly clearly from FIG. 1, the narrow, parallel-directed laser beam is widened out to form a narrow fan by cylindrical lens 38 acting at right angles to the above-indicated cylindrical lens 11. The narrow fanned out beam strikes the inside of crossed mirror 36. The reference letter $d$ designates the narrowest constriction of the laser beam in the focal line of cylindrical lens 38.

A tube of xenon lamp 33 has a larger cross-sectional areas which is reproduced in aperture 40, the height of aperture 40 being designated by reference lettter $a$.

According to the invention, the position of the smallest constriction $d$ and diaphragm 41 is selected in such a way that there is optically the same spacing from lens 42. Together lens 42 and concave mirror 48 reproduce on a larger scale dimensions $a$, $d$ according to FIG. 2 as linear extensions $a'$ and $d'$ in the scanning plane (material web) 12.

The illuminated width D on mirror wheel 43 due to the width dimensions of the laser beam or the axial length $b$ of the surfaces of mirror wheel 43 irradiated on all sides by the xenon lamp are reproduced on a reduced scale on material web 12 as dimensions D' or $b'$ by concave mirror 48 and cylindrical lens 11.

Thus, a smaller light spot 34 is formed by laser source 32 and a larger light spot 35 by xenon lamp 33. Due to the contraction of dimensions D and $b$ by cylindrical lens 11, the reproduction of the rectangular aperture 40 in light spot 35 is substantially square, whilst light spot 34 has the represented elliptical shape.

Preferably, the dimensions of the larger light spot 35 are as follows: $a' = 2$ mm; $b' = 2$ mm. Advantageous dimensions for the laser light spot are: $d' = 0.2$ mm; D' $= 2$ mm. The laser light spot 34 is approximately elliptical and is located centrally in spot 35 of the xenon lamp. Depending on the particular problem involved, these ratios can be changed.

In FIG. 4, 33' is the spectrum of xenon lamp 33. Filters 22, 29, 37 have the internal transmittance level indicated by the respective curve. Thus, only the spectral range of the xenon lamp light between about 200 and 700 nm and represented by continuous lines is transmitted to the photomultipliers 19 or 30. The other filter curve of FIG. 4 represents the internal transmittance level of red filters 21, 27 and shows that these filters substantially permit the passage of the radiation of an He-Ne laser at 633 nm. It is thus ensured that the photomultipliers 19 and 30 only receive the light of the selected spectral range of xenon lamp 33, whilst photomultipliers 18, 28 only receive laser light.

Thus, according to the invention, the signals reaching photomultipliers 18 and 28 can recognize very small faults, e.g., scratches. Photomultipliers 19 and 30 permit the recognition of larger, chromatic faults. The distinction between remitted light (light guide rod 14) and reflected light (light guide rod 13) also permits an additional differentiation, because different faults differently remit or reflect light.

Photomultipliers 18 and 28 also recognize larger faults if the correct spectral conditions exist.

According to a preferred embodiment, filter 22 in front of photomultiplier 19 can be removed so that the said photomultiplier receives remitted mixed light of laser light and filtered xenon light making it possible to recognize chromatic faults.

Figure 5:
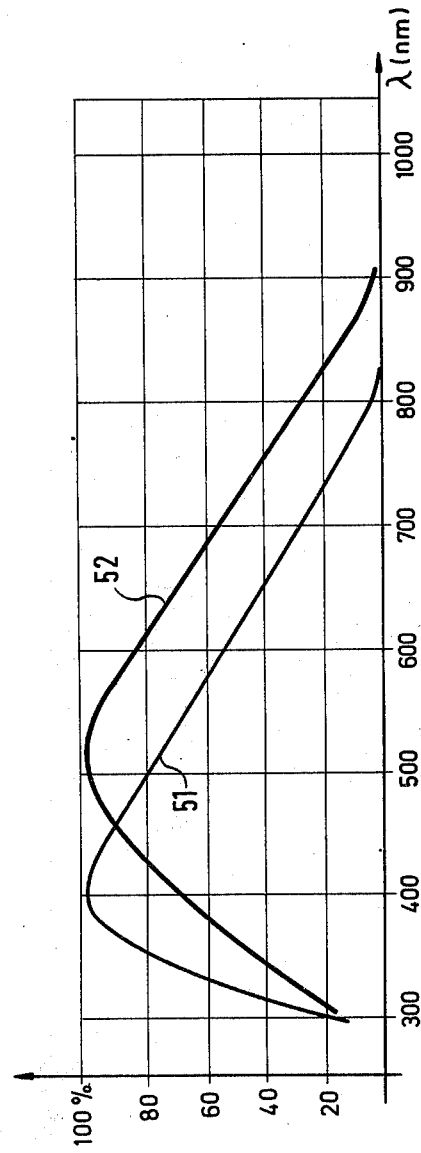
FIG. 5 a diagram of the relative spectral sensitivity of the photomultiplier used.

According to a simplified embodiment, light guide rod 14 and cylindrical lens 20 are omitted. The remitted mixed light consisting of laser light and xenon light is then deflected via the whole aperture of cylindrical lens 11, concave mirror 48, lens 42, crossed mirror 36 and a deflecting mirror 50 located at the place of diaphragm 41 onto a photomuliplier 31 which then also permits the recognition of chromatic faults. FIG. 5 shows the spectral sensitivity of the photomultipliers used in the different cases described. Sensitivity curve 51 applies for photomultiplier 31 and photomultiplier 19. Thus the particular photomultiplier is particularly suitable for receiving mixed light consisting of xenon light and laser light.

The spectral sensitivity curve 52 applies for photomultipliers 18 and 28 which receive the laser light. However, the photomultipliers which receive the xenon light can also have a spectral sensitivity curve 51.

The apparatus according to the invention functions as follows:

After switching on light sources 32 and 33, the light spots 34 and 35 according to FIG. 2 are reproduced in material web 12. By rotating mirror wheel 43 continuous scanning of the material web takes place in the direction of double arrow F from one side to the other. Simultaneously, material web 12 moves in the direction of arrow f. Thus, at photomultipliers 18, 19, 28 and 30 a total of four output signals are formed which can be electrically combined in any desired manner for emitting a signal which is characteristic of the scanned fault 26. The four signals received can also be evaluated separately. Thus, the invention provides a fault determination device which not only indicates the existence of a fault but also is able to supply four quantities enabling conclusions to be drawn on the nature of the fault detected, utilizing the different reaction of the individual faults to remitted or reflected light and to the light of different spectral ranges.

It is also important to point out that the xenon light is irradiated on all sides of the particular mirror wheel surface, whereas the laser beam striking the mirror wheel only has a larger extension than the mirror surface in the peripheral direction but is much narrower in the axial direction.

While there has been described and illustrated the preferred embodiments of the invention, it is to be understood that these are capable of variation and modification and it is therefore not desired to be limited to the precise details set forth but to include such modifications and alterations as fall within the scope of the appended claims.

What is claimed is:

1. Apparatus for inspecting a substantially flat surface portion of a material for faults which affect the remission and reflection of light incident on the material, the apparatus comprising: a first light source emitting light of a relatively narrow spectral band width; a second light source remitting light of a relatively broad spectral band width; means for projecting the light from the first and second light sources onto the material in the form of first and second, overlapping each other differing light spots, respectively; first and second light sensitive means for generating output signals responsive to light received and sensed by the light sensitive means; means for directing light from the spots on the material to the light sensitive means; and means for limiting the output signals of the first and second light sensitive means to light generated by the first and second light sources, respectively.

2. An apparatus according to claim 1 wherein the second light source is a xenon high pressure lamp.

3. Apparatus according to claim 1 wherein the light sources are substantially opposite from each other, and including a mirror having crossing reflecting surfaces positioned intermediate the light sources for directing light from the sources towards the web.

4. Apparatus according to claim 1 including a light sensitive device for emitting output signals responsive to light received by it from the first and the second light sources, and means for directing light from the first and second light spots remitted by the material to the light sensitive device.

5. An apparatus according to claim 1, wherein the first light source is a laser.

6. An apparatus according to claim 5, wherein the laser is an He-Ne gas laser.

7. Apparatus according to claim 1 wherein the means for directing light comprises a light conducting rod for capturing light from the spots and transmitting it to the light sensitive means.

8. Apparatus according to claim 7 wherein the second light source comprises a xenon high pressure lamp, and including a light filter positioned to intercept light emitted by the lamp and transmitting light in a spectral range of between about 200 to about 700 nm.

9. Apparatus according to claim 7 including a light filter interposed between the first light sensitive device and the corresponding light conducting rod end face, the filter transmitting light of a spectral band width substantially corresponding to the spectral band width of the first light source.

10. Apparatus according to claim 9 including another light filter interposed between the second light sensing means and the corresponding light conducting rod end face, said another filter separating light emitted by the first source from light emitted by the second source and transmitting the light from the second light source only.

11. Apparatus according to claim 7 including means for projecting light from the light spots reflected by the material to the light conducting rod.

12. Apparatus according to claim 11 including another light conducting rod, and means for projecting light from the light spots remitted by the material to said another light conducting rod.

13. Apparatus according to claim 12 including first and second light sensitive means in light communication with respective end faces of each of the light conducting rods.

14. An apparatus according to claim 1, wherein the first light spot is smaller than the second light spot and wherein the first spot is contained in the second spot.

15. An apparatus according to claim 14, wherein the second light spot is substantially rectangular.

16. An apparatus according to claim 15, wherein the first light spot is substantially elliptical.

17. An apparatus according to claim 16, wherein the large elliptical axis of the first spot is of approximately the same length as a side of the rectangular second light spot.

18. An apparatus according to claim 17, wherein the sides of the second spot and the elliptical axes of the first spot are parallel to one another.

19. Apparatus for inspecting a substantially flat surface portion of a material for faults which affect the remission and reflection of light incident on the material, the apparatus comprising: a first source emitting light of relatively narrow spectral band width; a second light source remitting light of a relatively broad spectral band width; means for projecting the light from the first and second light sources onto the material in the form of first and second overlapping light spots, respectively, the light spots differing from each other in at least one of their size and their shape; first and second light sensitive means for generating output signals responsive to light received by the light sensitive means; means for capturing light reflected by the light spots and for transmitting such light to the first and second light sensitive means; and means for limiting the output signals of the first and second light sensitive means to light reflected by the material from the first and the second light spots, respectively.

20. Apparatus according to claim 19 including means for capturing light remitted by the material from the first and second light spots; and at least one light sensitive device receiving captured light remitted by the material and generating other signals responsive to light from the first and second light sources and received and sensed by the device.

21. Apparatus according to claim 20 wherein the light sensitive device also includes third and fourth light sensitive means for generating said other signals; and including means for limiting said other signals generated by the other third and fourth light sensitive means to light generated by the first and second light sources, respectively.

22. Apparatus according to claim 21 wherein the means for capturing the remitted light and the reflected light comprises light conducting rods having end faces, wherein the first, second, third and fourth light sensitive means are optically coupled to end faces of the respective rods; and including means for projecting onto the respective rods the light reflected and the light remitted by the material from the first and second light spots.

* * * * *